United States Patent [19]

Klein et al.

[11] Patent Number: 4,869,873

[45] Date of Patent: Sep. 26, 1989

[54] MEASURING PROBE FOR DETERMINING VOLATILE CONSITITUENTS IN A LIQUID MEDIUM

[75] Inventors: Joachim Klein; Klaus-Dieter Vorlop, both of Brunswick; Jürgen W. Becke, Parsau, all of Fed. Rep. of Germany

[73] Assignee: Dr. W. Ingold AG, Urdorf, Switzerland

[21] Appl. No.: 20,907

[22] Filed: Aug. 2, 1987

[30] Foreign Application Priority Data

Mar. 4, 1986 [CH] Switzerland .................... 0871/86

[51] Int. Cl.⁴ .............................................. G01N 25/20
[52] U.S. Cl. ...................................... 422/51; 204/408; 422/78; 422/93
[58] Field of Search ................. 422/50, 51, 98, 56, 422/57, 68, 78, 93–95; 435/291; 73/25, 26; 204/403, 408

[56] References Cited

U.S. PATENT DOCUMENTS

| | | | |
|---|---|---|---|
| 4,404,284 | 9/1983 | Heider et al. | 435/291 |
| 4,415,878 | 11/1983 | Novak | 422/98 X |
| 4,433,982 | 2/1984 | Odernheimer et al. | 55/208 X |

FOREIGN PATENT DOCUMENTS

| | | |
|---|---|---|
| 0054537 | 6/1982 | European Pat. Off. . |
| 2913659 | 10/1980 | Fed. Rep. of Germany . |
| 3122662 | 4/1982 | Fed. Rep. of Germany . |
| 3126648 | 2/1986 | Fed. Rep. of Germany . |
| 1437075 | 5/1976 | United Kingdom . |
| 2088559 | 6/1982 | United Kingdom . |

*Primary Examiner*—Barry S. Richman
*Assistant Examiner*—T. J. Wallen
*Attorney, Agent, or Firm*—Werner W. Kleeman

[57] ABSTRACT

The measuring probe is equipped with a pellistor and renders possible directly determining in a trouble-free manner volatile constituents which are contained in a liquid medium to be investigated and which can be chemically converted with an accompanying heat effect. Heating devices are provided and, due to the prevention of condensate formation, greatly contribute to obtaining high measuring precision. The response time of the measuring probe can also be significantly reduced by heating a membrane which separates a measuring space containing the pellistor from the liquid medium to be investigated. The measuring probe can be used with advantage for monitoring microbiological processes, for example, in a fermenter.

13 Claims, 1 Drawing Sheet

MEASURING PROBE FOR DETERMINING VOLATILE CONSITITUENTS IN A LIQUID MEDIUM

BACKGROUND OF THE INVENTION

The present invention broadly relates to a new and improved construction of a measuring probe for determining at least one volatile constituent which is contained in a liquid medium and which can be chemically converted with an accompanying heat effect.

In its more particular aspects, the present invention specifically relates to a new and improved construction of a measuring probe for determining at least one volatile constituent which is contained in a liquid medium and which can be chemically converted with an accompanying heat effect, and which measuring probe contains a tubular casing or housing closed on one side by a membrane which is permeable for the at least one volatile constituent. In its interior, the tubular casing or housing contains a concentrically arranged internal body or member and a detector which responds to temperature changes and which constitutes a pellistor. The pellistor is constructed from an electric heating element, specifically a platinum wire which can be connected to a power source, and a matrix into which the electrical heating element is embedded. The pellistor further contains a surface coating containing an oxidation catalyst. The nature of the pellistor is such that the pellistor emits or generates electrical measuring signals as a function of the aforementioned temperature changes.

When carrying out microbiological or food technology processes, it is frequently necessary for monitoring and controlling such processes, to determine the content of volatile constituents, particularly lower alcohols such as methanol and ethanol in the medium under investigation. The content of these constituents provides information, for example, with respect to the progress of a fermentation process or the alcohol content of a liquid, for example, a beverage.

The determination of alcohols, particularly ethanol, as volatile constituents of culture media in fermenters hitherto generally was effected using gas chromatography, mass spectrometry or by means of flame ionization detectors. The amount of time and work necessary for carrying out these determinations is relatively great so that there exists a considerable demand for simpler and less costly methods.

It is further known to flush the volatile constituents out of the fermenter by means of a carrier gas, for example, air or nitrogen and pass the thus obtained gas mixture along a heated platinum wire coil. During such passage, the volatile constituents, for example, alcohol are subjected to oxidation.

It is also known to employ semiconductor elements for determining oxidizable gases in containers for combustible liquids, for example, in fuel tanks. Such semiconductor elements experience a resistance change due to the temperature change caused by the absorption of the volatile constituents at the semiconductor surface. However, due to the insufficient linearity and the complicated pre-treatment or preconditioning, it is impractical to use such semiconductor elements as detectors for the quantitative determination of alcohols present in the liquid phase.

In addition, there are known gas sensors which contain as the essential component a pellistor in which a metallic filament is surrounded by a metal oxide coated and/or impregnated with a catalyst material. These gas sensors are mainly used for monitoring the air and are sensitive to the action of thermal shocks and condensate formation so that their use is limited to a relatively narrow field.

SUMMARY OF THE INVENTION

Therefore, with the foregoing in mind, it is a primary object of the present invention to provide a new and improved construction of a measuring probe for determining at least one volatile constituent which is contained in a liquid medium and which can be chemically converted with an accompanying heat effect, and which measuring probe does not exhibit the drawbacks and shortcomings of prior art constructions.

A further significant object of the present invention aims at providing a new and improved construction of a measuring probe for determining at least one volatile constituent in a liquid medium and of the character described and which measuring probe is relatively simple in construction and design, extremely economical to manufacture, highly reliable in operation, not readily subject to breakdown or malfunction and requires a minimum of maintenance and servicing.

Another important object of the present invention is directed to a new and improved construction of a measuring probe for determining at least one volatile constituent which is contained in a liquid medium and which can be chemically converted with an accompanying heat effect, and which measuring probe, although being of simple construction and operating with comparatively small amounts of time and work, permits the at least one volatile constituent to be quantitatively determined at high precision.

Another and more specific object of the present invention aims at providing a new and improved construction of a measuring probe for determining at least one volatile constituent which is contained in a liquid medium and which can be chemically converted with an accompanying heat effect, and which measuring probe generates measured values which can be used for process control purposes.

Still a further significant object of the present invention is directed to a new and improved construction of a measuring probe for determining at least one volatile constituent which is contained in a liquid medium and which can be chemically converted with an accompanying heat effect, and which measuring probe can be reliably operated without using a carrier gas.

Another, still important object of the present invention, is directed to a new and improved construction of a measuring probe for determining at least one volatile constituent which is contained in a liquid medium and which can be chemically converted with an accompanying heat effect, and which measuring probe can be operated without the necessity of frequent recalibrations.

Now in order to implement these and still further objects of the invention which will become more readily apparent as the description proceeds, the measuring probe of the present development is manifested by the features that, the pellistor is mounted or fixed at the internal body or member and arranged within a measuring space or chamber which is closed by the membrane. The internal body or member contains diffusion channels or ducts extending in longitudinal direction of the internal body or member and opening into the measuring space or chamber. Heating means or devices are provided for heating the membrane and/or the internal body or member.

It is a particular advantage that in the inventive measuring probe, the pellistor serves as the detector under conditions under which the pellistor constitutes a robust resistance element which is largely independent of chemical or thermal influences. The nature of this resistance element is such that the occurring temperature change is converted into a resistance change according to a linear relationship between the temperature change and the resistance change. Since the temperature change, in turn, is directly dependent upon the heat effect accompanying the chemical conversion or reaction, the measuring probe renders possible directly determining the concentration of the at least one volatile constituent on the basis of the measured resistance values.

The nature of the pellistor further makes it possible to provide a specific detector for the volatile constituent to be determined in each individual case. By embedding into a matrix the platinum wire, which can be heated to a given temperature by applying a given power, there is achieved the beneficial effect that there can be avoided malfunctions which, in the known arrangements, can be attributed to poisoning of the platinum. The surface coating using a specific catalyst material, for example, precious metal ensures the complete conversion of the volatile constituent to be determined in each individual case.

The resistance values either can be read off or recorded by a suitable measuring instrument. However, also in the case of a microbiological process, the resistance values can be supplied to a microprocessor for controlling the reaction in the fermenter.

Due to the fact that the pellistor is arranged within the measuring space or chamber which is closed by the membrane permitting throughpassage of the volatile constituents present in the medium to be investigated and into which open the diffusion channels or ducts present in the internal body or member, there is obtained the favorable effect that the volatile constituents quantitatively pass to the pellistor surface. The diffusion channels or ducts are generally dimensioned such that there is ensured a sufficient supply of a gas, particularly oxygen-containing gas to the surface of the pellistor and which gas is required for the chemical conversion or reaction, particularly oxidation of the volatile constituent to be determined. The diffusion channels or ducts extend substantially through the entire length of the internal body or member and communicate with the environmental atmosphere by openings present in a part of the tubular casing and which part is located opposite to the membrane Heating means or devices are provided for heating the membrane and/or the internal body or member of the measuring probe and substantially completely prevent the occurrence of condensates which would impair the precision of measurement.

The measuring probe is especially suitable for determining alcohols such as appear as volatile constituents of culture media in fermentation processes and constitute an important indicator indicating the course of the fermentation process. The oxidation catalyst of the pellistor surface coating enables quantitative oxidation of volatile alcohols. These alcohols are oxidized to carbon dioxide and water. The heat of oxidation produced during the oxidation, results in a change in the pellistor temperature and thus in a measurable change in the pellistor resistance. There exists a linear relationship between the alcohol concentration and the voltage change or drop caused by the resistance change. In analogous manner, there can also be determined, for example, the alcohol content of other liquids, for example, beverages. The use of measuring probes containing a pellistor having a surface coating which contains an oxidation catalyst, however, is not limited to the determination of alcohols but is also possible for the determination of other oxidizable substances in analogous manner.

Preferably the inventive measuring probe contains a plurality of diffusion channels or ducts arranged in the interior of the internal body or member and permitting gas exchange between the measuring space or chamber and the environmental atmosphere surrounding the tubular casing. There is thus achieved an especially advantageous gas exchange between the measuring space or chamber and the ambient atmosphere. Due to the inward diffusion of gas, particularly oxygen-containing gas, generally air from the ambient atmosphere, there is obtained a sufficient oxygen supply to the measuring space or chamber and in particular at the pellistor surface so that a quantitative chemical conversion is ensured.

Advantageously, the membrane in the inventive measuring probe can be heated by means of a heatable membrane carrier. Such arrangement is advantageous in view of the prevention of condensate formation in the measuring space or chamber because, due to the heating of the membrane by means of the heatable membrane carrier, the temperature of the membrane and the temperature inside the measuring space or chamber can be set to a value above the condensation temperature. Furthermore, the response time of the measuring probe is reduced to a significant extent through heating the membrane.

In an advantageous construction of the inventive measuring probe, a heating means or device, for example, a heating rod is arranged within the internal body or member and is constructed such as to permit substantially uniform heating of the diffusion channels or ducts to a temperature which prevents condensate formation. There is thus rendered possible preheating the inwardly diffusing gas, preferably oxygen-containing gas, to a temperature which prevents condensate formation in the measuring space or chamber as well as in the diffusion channels or ducts. Moreover, due to the arrangement of the heating means or device in the internal body or member, a temperature rise is achieved within the measuring space or chamber and also contributes to preventing condensate formation. The heating means or device may constitute, for example, a heating rod which is inserted into the internal body or member and which at least partly extends therethrough.

In a further preferable construction of the inventive measuring probe, the internal body or member is made from a material such as, in particular, metals and metal alloys having a high thermal conductivity. Such materials lead to the advantage that the heat which is supplied by means of the heating device arranged in the internal body or member, is distributed substantially without delay and substantially throughout the entire internal body or member, so that there is ensured substantially uniform heating of the diffusion channels or ducts for the gas. Particularly, there is ensured substantially uniform heating and temperature balance or equalization substantially without delay and substantially throughout the entire internal body or member.

According to a further advantageous construction, temperature sensors and/or associated control means can be provided in the inventive measuring probe for measuring and/or controlling the temperature of the internal body or member and/or the membrane carrier. There is thus achieved precise monitoring and/or control of the temperature of the internal body or member and/or the membrane carrier. The measured value supplied by the temperature sensors, if desired, can be used for controlling the heating circuits for the heating means or device for the internal body or member and/or the membrane carrier via a central control unit, for example, a microprocessor.

In a further advantageous construction of the inventive measuring probe, control means are provided for controlling the temperature of the pellistor. Such construction permits specific adaptation to the volatile constituents to be determined in each individual case. When the measuring probe, for example, is used for determining alcohols, then, the same pellistor can be used for ethanol as well as for methanol and merely the pellistor temperature must be correspondingly set. The temperatures to be set in each individual case, can be determined without difficulty mathematically or by preliminary tests.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Figure 1:
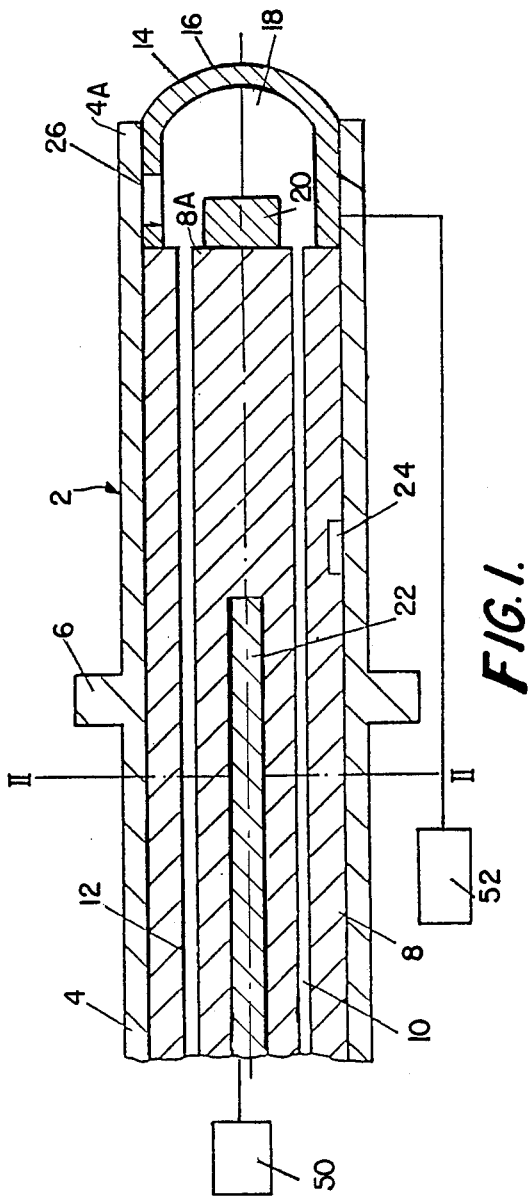
FIG. 1 shows a schematic, fragmentary longitudinal section of an exemplary embodiment of the inventive measuring probe.

Describing now the drawings, it is to be understood that to simplify the showing thereof, only enough of the structure of the measuring probe has been illustrated therein as is needed to enable one skilled in the art to readily understand the underlying principles and concepts of the present invention. Turning now specifically to FIG. 1 of the drawings, the measuring probe illustrated therein by way of example and not limitation, will be seen to comprise a measuring probe 2 of the type advantageously used for monitoring microbiological processes in a fermenter. Such measuring probe 2 contains a tubular casing or housing 4 provided with a flange 6 by means of which the measuring probe 2 can be mounted or fixed at a suitable connecting piece provided in the wall of a fermenter.

An internal body or member 8 containing diffusion channels or ducts 10 and 12, is fitted into the tubular casing 4 and arranged substantially coaxially with and in the longitudinal direction of the tubular casing 4. In a section of the measuring probe 2 and which section is intended to be immersed into a liquid or solution to be investigated, the tubular casing 4 projects beyond the internal body or member 8 and is closed at one end 4A by a membrane 14 which is permeable for the volatile constituent to be determined, for example, ethanol and constitutes, for example, a Teflon membrane. The membrane 14 is fixed to one end 8A of the internal body or member 8 by means of a preferably heatable membrane carrier 16 and arranged such that the associated opening or one end 4A of the tubular casing 4 is tightly sealed.

The membrane 14, the membrane carrier 16 and the surface or one end 8A of the internal body or member 8 facing the membrane 14 surround or define an actual measuring space or chamber 18 in which a pellistor 20 is arranged. The pellistor 20 can be mounted or fixed either directly in a depression formed at the one end 8A of the internal body or member 8 or by means of a base member. The diffusion channels or ducts 10 and 12 open into the measuring space or chamber 18 at this one pellistor carrying end 8A of the internal body 8. From the entry point thereof into the measuring space or chamber 18, the diffusion channels or ducts 10 and 12 extend substantially through the entire length of the internal body or member 8 and are in communication with the surrounding atmosphere by means of openings which are provided in the tubular casing 4 in a head section not shown in the drawing. The number and dimensions of the diffusion channels or ducts 10 and 12 are selected such that there can be effected an unimpeded gas exchange between the measuring space or chamber 18 and the surrounding atmosphere. Consequently, there is ensured a sufficient supply of gas, in particular an adequate oxygen supply, to the pellistor 20 as required for the chemical conversion or reaction.

Within the internal body or member 8 there is arranged a heating means or device in the form of a heating rod 22 which extends at least through a part of the internal body or member 8. The heating rod 22 serves to heat the internal body or member 8 to a temperature ensuring that at least the oxygen-containing gas flowing through the diffusion channels or ducts 10 and 12 to the measuring space or chamber 18, is heated to such an extent that its temperature is higher than that of the membrane 14 and the investigated liquid or solution into which the measuring probe 2 is immersed during the investigation. In order to ensure a substantially uniform temperature distribution within the internal body or member 8, this internal body or member 8 appropriately is made from a material possessing high heat conductivity.

A temperature sensor 24 and operatively associated control means 50 are provided for monitoring and controlling the temperature of the internal body or member 8. The heatable membrane carrier 16 is equipped with a temperature sensor 26 which is operatively connected to control means 52 for monitoring and controlling the temperature of the membrane 14. The measured values supplied by the temperature sensors 24 and 26 can also be fed to a central control unit, for example, a microprocessor and used for controlling the temperature of the heating rod 22 and the heatable membrane carrier 16.

In general, the internal body or member 8 further contains throughpassages for heating current conductors or lines connecting the pellistor 20 to a power supply 34, as well as measuring lines 40 leading from the pellistor 20 to a measuring instrument 42 or to control means 54. Connecting elements for such lines are generally housed in the section opposite to the measuring space or chamber 18, i.e. the not specifically illustrated head section of the measuring probe 2.

Figure 2:
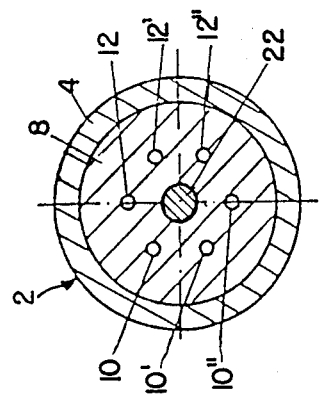
FIG. 2 show a cross-section along the line II-II in FIG. 1 through the measuring probe shown in FIG. 1.

The cross-section of the inventive measuring probe 2 as shown in FIG. 2 illustrates a construction in which a plurality of diffusion channels or ducts 10, 10', 10'', 12, 12' and 12'' is arranged in the internal body or member 8 accommodated in the tubular casing 4. The provision of the plurality of diffusion channel or ducts 10, 10', 10'', 12, 12' and 12'' permits a particularly high throughput, in particular of oxygen-containing gas and thus a substantially complete chemical conversion or reaction at the pellistor surface of the volatile or gaseous constituents entering the measuring space or chamber 18 through the membrane 14. The selection of the number and dimensions, in particular, the internal diameter of the diffusion channels or ducts 10, 10', 10'', 12, 12' and 12'' is predicated upon the oxygen requirements of the chemical conversion or reaction taking place at the pellistor 20 and can be determined either mathematically or by preliminary tests. The centrally arranged heating rod 22 makes it possible to heat the internal body or member 8 and thereby the gas diffusing through the diffusion channels or ducts 10, 10', 10'', 12, 12' and 12''.

Figure 3:
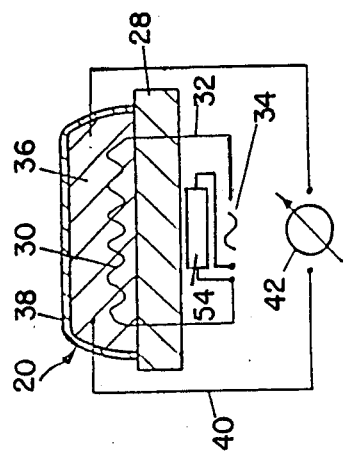
FIG. 3 is a section through a pellistor used in the measuring probe shown in FIG. 1.

FIG. 3 shows a section through a pellistor 20 of the type as preferably used for determining the ethanol concentration in a culture medium contained in a fermenter. The pellistor 20, which is arranged on a base 28, contains an electric heating element constituting a platinum wire coil 30 which can be connected by means of heating current conductors 32 to a power supply 34 and can be heated to a predetermined temperature. The platinum wire coil 30 is embedded into a matrix 36, for example, of alumina. Furthermore, the pellistor 20 possesses a surface coating 38 containing an oxidation catalyst. The pellistor 20 also is equipped with measuring lines or conductors 40 for connection to a measuring instrument 42 from which there can be read the voltage change or drop caused by the resistance change. Additionally, there can be further provided control means 54 for controlling the temperature of the pellistor 20.

When carrying out a measurement for determining the alcohol content in a culture medium, the measuring probe 2 is immersed, for example, into a fermenter containing the culture medium. The measuring probe 2 is mounted or fixed by means of the flange 6 of the tubular casing 4 at a connecting piece located in the fermenter wall. In order to prevent the formation of condensates in the measuring space or chamber 18 due to the different temperatures of the gas, for example, air and the ethanol originating from the culture medium, the internal body or member 8 is heated to approximately 130° C by means of the heating rod 22. The vaporous alcohol taken up and entrained by the gas is oxidized to carbon dioxide and water at the surface of the pellistor 20 which is heated to a predetermined temperature of, for example, 250° C.

By suitably selecting the temperature of the pellistor 20 and the number and size of the diffusion channels or ducts in the internal body or member 8 there is effected quantitative oxidation of the ethanol. The temperature of the pellistor 20 is increased by the released heat of oxidation so that there results a change in the resistance of the pellistor 20. The electrical measuring signals resulting from the resistance change pass to a voltmeter where they can be read or recorded. However, it is also possible to directly feed the obtained electrical measuring signals to a central control unit, for example, a microprocessor by means of which a control of the fermentation process can be effected.

While there are shown and described present preferred embodiments of the invention, it is to be distinctly understood that the invention is not limited thereto, but may be otherwise variously embodied and practiced within the scope of the following claims. ACCORDINGLY,

What we claim is:

1. A measuring probe for determining at least one volatile constituent which is contained in a liquid medium and which can be chemically converted with an accompanying negative or positive heat of conversion, comprising:

a tubular casing having one end;

a membrane sealingly closing said one end of said tubular casing;

an internal body concentrically arranged and longitudinally extending in said tubular casing and defining one end facing said membrane;

said one end of said internal body and said membrane bounding a space at said one end of said tubular casing;

said membrane being adapted to be throughpassed by said at least one volatile constituent in the vaporous state when said membrane is immersed into a liquid medium containing said at least one volatile constituent;

a pellistor fixed at said one end of said internal body within said space;

said pellistor being located directly opposite said membrane and thereby being directly exposed to said at least one vaporous volatile constituent which has passed through said membrane;

said pellistor constituting a detector responsive to temperature changes due to the heat of conversion accompanying the chemical conversion of said at least one vaporous volatile constituent at said pellistor;

a power source;

said pellistor containing an electric heating element connectable to said power source for heating said pellistor to a predetermined operating temperature;

said pellistor further containing a matrix into which said electric heating element is embedded;

said matrix of said pellistor being provided with a surface coating exposed to said at least one vaporous volatile constituent and containing a catalyst catalyzing said chemical conversion of said at least one vaporous volatile constituent at said predetermined operating temperature of said pellistor;

said catalyst constituting an oxidation catalyst catalyzing the oxidation of said at least one vaporous volatile constituent to gaseous oxidation products at said predetermined operating temperature of said pellistor and thereby producing temperature changes due to the heat of oxidation of said at least one vaporous volatile constituent;

said internal body containing at least one diffusion channel extending longitudinally through said internal body;

said at least one diffusion channel opening at said one end of said internal body directly opposite said membrane into said space at said one end of said tubular casing;

said at least one diffusion channel communicating with the environmental atmosphere surrounding said tubular casing, for providing a gas exchange between said space, which is bounded by said one end of said internal body and said membrane at said one end of said tubular casing, and the environmental atmosphere; and heating means for selectively heating at least one of said membrane and said internal body.

2. The measuring probe as defined in claim 1, wherein:

said heating means serves for heating said internal body for preventing condensation of said at least one vaporous volatile constituent from said space onto said internal body.

3. The measuring probe as defined in claim 2, wherein:

said heating means for heating said internal body are arranged within said internal body; and said heating means being arranged such as to permit substantially uniform heating of said at least one diffusion channel to a temperature which prevents condensate formation.

4. The measuring probe as defined in claim 3, wherein:

said heating means arranged within said internal body constitute a heating rod.

5. The measuring probe as defined in claim 3, wherein:

said internal body is made form a material having a predetermined high thermal conductivity; and said predetermined high thermal conductivity of said internal body ensuring rapid temperature equalization substantially throughout the entire internal body when heated by said heating means.

6. The measuring probe as defined in claim 2, further including:

a temperature sensor for measuring the temperature of said internal body.

7. The measuring probe as defined in claim 6, further including:

control means for controlling the temperature of said internal body such a to prevent said condensation of said at least one vaporous volatile constituent from said space onto said internal body; and said temperature sensor being electrically connected to said control means.

8. The measuring probe as defined in claim 1, wherein:

said heating means for heating said permeable membrane for preventing condensation of said at least one vaporous volatile constituent from said space onto said membrane.

9. The measuring probe as defined in claim 8, further including:

a membrane carrier supporting said permeable membrane; and said membrane carrier constituting a heatable membrane carrier serving at least as part of said heating means for heating said permeable membrane in order to prevent said condensation of said at least one vaporous volatile constituent from said space onto said membrane.

10. The measuring probe as defined in claim 9, further including:

a temperature sensor for measuring the temperature of said membrane carrier.

11. The measuring probe as defined in claim 10, further including:

control means for controlling the temperature of said membrane carrier such as to prevent said condensation of said at least one vaporous volatile constituent from said space onto said membrane; and said temperature sensor being connected to said control means.

12. The measuring probe as defined in claim 1, wherein:

said internal body contains, as said at least one diffusion channel, a plurality of diffusion channels for providing said gas exchange between said space, which is bound by said one end of the internal body and said membrane at said one end of said tubular casing, and the environmental atmosphere, and which plurality of diffusion channels opens into said space at said one pellistor carrying end of said internal body directly opposite said membrane.

13. A measuring probe for determining at least one volatile constituent which is contained in a liquid medium, comprising:

a tubular casing having one end;

a membrane sealingly closing said one end of said tubular casing;

an internal body concentrically arranged and longitudinally extending in said tubular casing and defining one end facing said membrane;

said one end of said internal body and said membrane bounding a space at said one end of said tubular casing;

said membrane being adapted to be throughpassed by said at least one volatile constituent in the vaporous state when said membrane is immersed into a said liquid medium containing said at least one volatile constituent;

a pellistor fixed at said one end of said internal body within said space;

said pellistor being located directly opposite said membrane and thereby being directly exposed to said at least one vaporous volatile constituent which has passed through said membrane;

a power source;

said pellistor containing an electric heating element connectable to said power source for heating said pellistor to a predetermined operating temperature and for oxidizing the at least one vaporous volatile constituent which has passed through the membrane;

said internal body containing at least one channel extending longitudinally through said internal body;

said at least one channel opening at said one end of said internal body directly opposite said membrane into said space at said one end of said tubular casing in order to provide an oxidizing atmosphere in the space at said one end of said tubular casing; and;

heating means for selectively heating at least one of said membrane and said internal body.

* * * * *

UNITED STATES PATENT AND TRADEMARK OFFICE
CERTIFICATE OF CORRECTION

PATENT NO. : 4,869,873

DATED : September 26, 1989

INVENTOR(S) : JOACHIM KLEIN et al

It is certified that error appears in the above-identified patent and that said Letters Patent is hereby corrected as shown below:

On the title page, item [54], please amend the title by deleting "CONSITITUENTS" and insert --CONSTITUENTS--

On the title page, item [75], line 2, please delete "Brunswick" and insert --Braunschweig--

On the title page, item [22], please amend to read --March 2, 1987--

Column 1, line 2, please delete "CONSITITUENTS" and insert --CONSTITUENTS--

Column 3, line 29, after "complete" please insert --chemical--

Column 9, line 31, after "made" please delete "form" and insert --from--

Column 9, line 44, after "such" please delete "a" and insert --as--

Column 9, line 51, after "means" please insert --serves--

UNITED STATES PATENT AND TRADEMARK OFFICE
CERTIFICATE OF CORRECTION

PATENT NO. : 4,869,873

DATED : September 26, 1989

INVENTOR(S) : JOACHIM KLEIN et al

It is certified that error appears in the above-identified patent and that said Letters Patent is hereby corrected as shown below:

Column 10, line 38, after "a" please delete "said"

Signed and Sealed this

Twenty-seventh Day of November, 1990

*Attest:*

HARRY F. MANBECK, JR.

*Attesting Officer*  *Commissioner of Patents and Trademarks*